United States Patent
Kugler et al.

(10) Patent No.: US 12,214,144 B2
(45) Date of Patent: Feb. 4, 2025

(54) ENDOVASCULAR DEVICES AND METHODS

(71) Applicant: BOSTON SCIENTIFIC SCIMED, INC., Maple Grove, MN (US)

(72) Inventors: Chad J. Kugler, Buffalo, MN (US); Robert E. Atkinson, Lake Elmo, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 18/370,453

(22) Filed: Sep. 20, 2023

(65) Prior Publication Data

US 2024/0001085 A1 Jan. 4, 2024

Related U.S. Application Data

(63) Continuation of application No. 17/547,442, filed on Dec. 10, 2021, now Pat. No. 11,793,978, which is a
(Continued)

(51) Int. Cl.
| | |
|---|---|
| *A61M 25/09* | (2006.01) |
| *A61B 17/22* | (2006.01) |
| *A61M 25/10* | (2013.01) |

(52) U.S. Cl.
CPC ... *A61M 25/09* (2013.01); *A61B 2017/22095* (2013.01); *A61M 2025/09083* (2013.01);
(Continued)

(58) Field of Classification Search
CPC ............... A61M 25/09; A61M 25/104; A61M 2025/09083; A61M 2025/09133;
(Continued)

(56) References Cited

U.S. PATENT DOCUMENTS

| | | | |
|---|---|---|---|
| 4,020,829 A | 5/1977 | Wilson et al. | |
| 4,233,983 A | 11/1980 | Rocco | |

(Continued)

FOREIGN PATENT DOCUMENTS

| | | |
|---|---|---|
| WO | 0178822 A2 | 10/2001 |
| WO | 2007033052 A2 | 3/2007 |

(Continued)

OTHER PUBLICATIONS

Bolia, Amman, "Subintimal Angioplasty: Which Cases to Choose, How to Avoid Pitfalls and Technical Tips." Combined Session: Vascular Surgery and Interventional Radiology, pp. III 8. 1-III 8.3.
(Continued)

*Primary Examiner* — Phillip A Gray
(74) *Attorney, Agent, or Firm* — Seager, Tufte & Wickhem LLP

(57) ABSTRACT

Devices and methods for the treatment of chronic total occlusions are provided. One disclosed embodiment comprises a method of facilitating treatment via a vascular wall defining a vascular lumen containing an occlusion therein. The method includes providing an intravascular device having a distal portion with a lumen extending therein; inserting the device into the vascular lumen; positioning the distal portion in the vascular wall; and directing the distal portion within the vascular wall.

20 Claims, 10 Drawing Sheets

Related U.S. Application Data continuation of application No. 16/396,171, filed on Apr. 26, 2019, now Pat. No. 11,229,776, which is a continuation of application No. 13/037,797, filed on Mar. 1, 2011, now Pat. No. 10,315,010, which is a continuation of application No. 11/518,521, filed on Sep. 11, 2006, now Pat. No. 7,918,870.

(60) Provisional application No. 60/716,287, filed on Sep. 12, 2005.

(52) U.S. Cl.
CPC ............. *A61M 2025/09133* (2013.01); *A61M 2025/09175* (2013.01); *A61M 2025/09191* (2013.01); *A61M 25/104* (2013.01)

(58) Field of Classification Search
CPC ......... A61M 2025/09175; A61M 2025/09191; A61B 2017/22095
USPC ....................................................... 606/159
See application file for complete search history.

(56) References Cited

U.S. PATENT DOCUMENTS

| | | |
|---|---|---|
| 4,569,347 A | 2/1986 | Frisbie |
| 4,581,017 A | 4/1986 | Sahota |
| 4,621,636 A | 11/1986 | Fogarty |
| 4,747,821 A | 5/1988 | Kensey et al. |
| 4,762,130 A | 8/1988 | Fogarty et al. |
| 4,774,949 A | 10/1988 | Fogarty |
| 4,819,634 A | 4/1989 | Shiber |
| 4,878,495 A | 11/1989 | Grayzel |
| 4,976,689 A | 12/1990 | Buchbinder et al. |
| 4,979,939 A | 12/1990 | Shiber |
| 4,990,134 A | 2/1991 | Auth |
| 5,071,406 A | 12/1991 | Jang |
| 5,127,917 A | 7/1992 | Niderhauser et al. |
| 5,193,546 A | 3/1993 | Shaknovich |
| 5,201,753 A | 4/1993 | Lampropoulos et al. |
| 5,263,493 A | 11/1993 | Avitall |
| 5,275,610 A | 1/1994 | Eberbach |
| 5,324,263 A | 6/1994 | Kraus et al. |
| 5,342,301 A * | 8/1994 | Saab ....................... A61F 7/123 604/103.13 |
| 5,356,418 A | 10/1994 | Shturman |
| 5,372,587 A | 12/1994 | Hammerslag et al. |
| 5,383,856 A | 1/1995 | Bersin |
| 5,385,152 A | 1/1995 | Abele et al. |
| 5,409,453 A | 4/1995 | Lundquist et al. |
| 5,415,637 A | 5/1995 | Khosravi |
| 5,464,395 A | 11/1995 | Faxon et al. |
| 5,501,667 A | 3/1996 | Verduin, Jr. |
| 5,505,702 A | 4/1996 | Arney |
| 5,534,007 A | 7/1996 | St. Germain et al. |
| 5,555,883 A | 9/1996 | Avitall |
| 5,565,583 A | 10/1996 | Frank et al. |
| 5,571,122 A | 11/1996 | Kelly et al. |
| 5,571,169 A | 11/1996 | Plaia et al. |
| 5,603,720 A | 2/1997 | Kieturakis |
| 5,643,298 A | 7/1997 | Nordgren et al. |
| 5,645,529 A | 7/1997 | Fagan et al. |
| 5,655,548 A | 8/1997 | Nelson et al. |
| 5,695,506 A | 12/1997 | Pike et al. |
| 5,728,133 A | 3/1998 | Kontos |
| 5,741,270 A | 4/1998 | Hansen et al. |
| 5,741,429 A | 4/1998 | Donadio, III et al. |
| 5,779,721 A | 7/1998 | Nash |
| 5,807,241 A | 9/1998 | Heimberger |
| 5,824,071 A | 10/1998 | Nelson et al. |
| 5,830,222 A | 11/1998 | Makower |
| 5,830,224 A | 11/1998 | Cohn et al. |
| 5,843,050 A | 12/1998 | Jones et al. |
| 5,910,133 A | 6/1999 | Gould |
| 5,916,194 A | 6/1999 | Jacobsen et al. |
| 5,935,108 A | 8/1999 | Katoh et al. |
| 5,944,686 A | 8/1999 | Patterson et al. |
| 5,954,713 A | 9/1999 | Newman et al. |
| 5,957,900 A | 9/1999 | Ouchi |
| 5,968,064 A | 10/1999 | Selmon et al. |
| 5,989,276 A | 11/1999 | Houser et al. |
| 6,010,449 A | 1/2000 | Selmon et al. |
| 6,013,055 A | 1/2000 | Bampos et al. |
| 6,015,405 A | 1/2000 | Schwartz et al. |
| 6,022,343 A | 2/2000 | Johnson et al. |
| 6,036,707 A | 3/2000 | Spaulding |
| 6,036,717 A | 3/2000 | Mers Kelly et al. |
| 6,059,750 A | 5/2000 | Fogarty et al. |
| 6,068,638 A | 5/2000 | Makower |
| 6,071,281 A | 6/2000 | Burnside et al. |
| 6,071,292 A | 6/2000 | Makower et al. |
| 6,081,738 A | 6/2000 | Hinohara et al. |
| 6,099,542 A | 8/2000 | Cohn et al. |
| 6,117,064 A | 9/2000 | Apple et al. |
| 6,120,516 A | 9/2000 | Selmon et al. |
| 6,126,649 A | 10/2000 | VanTassel et al. |
| 6,155,264 A | 12/2000 | Ressemann et al. |
| 6,157,852 A | 12/2000 | Selmon et al. |
| 6,159,225 A | 12/2000 | Makower |
| 6,183,432 B1 | 2/2001 | Milo |
| 6,186,972 B1 | 2/2001 | Nelson et al. |
| 6,190,353 B1 | 2/2001 | Makower et al. |
| 6,203,559 B1 | 3/2001 | Davis et al. |
| 6,217,527 B1 | 4/2001 | Selmon et al. |
| 6,217,549 B1 | 4/2001 | Selmon et al. |
| 6,221,049 B1 | 4/2001 | Selmon et al. |
| 6,231,546 B1 | 5/2001 | Milo et al. |
| 6,231,587 B1 | 5/2001 | Makower |
| 6,235,000 B1 | 5/2001 | Milo et al. |
| 6,241,667 B1 | 6/2001 | Vetter et al. |
| 6,246,914 B1 | 6/2001 | de la Rama et al. |
| 6,254,588 B1 | 7/2001 | Jones et al. |
| 6,254,598 B1 | 7/2001 | Edwards et al. |
| 6,258,052 B1 | 7/2001 | Milo |
| 6,266,550 B1 | 7/2001 | Selmon et al. |
| 6,277,133 B1 | 8/2001 | Kanesaka |
| 6,283,940 B1 | 9/2001 | Mulholland |
| 6,283,951 B1 | 9/2001 | Flaherty et al. |
| 6,283,983 B1 | 9/2001 | Makower et al. |
| 6,287,317 B1 | 9/2001 | Makower et al. |
| 6,302,875 B1 | 10/2001 | Makower et al. |
| 6,330,884 B1 | 12/2001 | Kim |
| 6,337,142 B2 | 1/2002 | Harder et al. |
| 6,358,244 B1 | 3/2002 | Newman et al. |
| 6,375,615 B1 | 4/2002 | Flahery et al. |
| 6,379,319 B1 | 4/2002 | Garibotto et al. |
| 6,387,119 B2 | 5/2002 | Wolf et al. |
| 6,398,798 B2 | 6/2002 | Selmon et al. |
| 6,416,523 B1 | 7/2002 | Lafontaine |
| 6,428,552 B1 | 8/2002 | Sparks |
| 6,432,127 B1 | 8/2002 | Kim et al. |
| 6,447,539 B1 | 9/2002 | Nelson et al. |
| 6,475,226 B1 | 11/2002 | Belef et al. |
| 6,485,458 B1 | 11/2002 | Takahashi |
| 6,491,660 B2 | 12/2002 | Guo et al. |
| 6,491,707 B2 | 12/2002 | Makower et al. |
| 6,506,178 B1 | 1/2003 | Schubart et al. |
| 6,508,824 B1 | 1/2003 | Flaherty et al. |
| 6,508,825 B1 | 1/2003 | Selmon et al. |
| 6,511,458 B2 | 1/2003 | Milo et al. |
| 6,514,217 B1 | 2/2003 | Selmon et al. |
| 6,544,230 B1 | 4/2003 | Flaherty et al. |
| 6,561,998 B1 | 5/2003 | Roth et al. |
| 6,565,583 B1 | 5/2003 | Deaton et al. |
| 6,569,143 B2 | 5/2003 | Alchas et al. |
| 6,569,145 B1 | 5/2003 | Scmulewitz et al. |
| 6,569,150 B2 | 5/2003 | Teague et al. |
| 6,579,311 B1 | 6/2003 | Makower |
| 6,589,164 B1 | 7/2003 | Flaherty |
| 6,599,304 B1 | 7/2003 | Selmon et al. |
| 6,602,241 B2 | 8/2003 | Makower et al. |
| 6,613,081 B2 | 9/2003 | Kim et al. |
| 6,616,675 B1 | 9/2003 | Evard et al. |

(56) References Cited

U.S. PATENT DOCUMENTS

| | | | |
|---|---|---|---|
| 6,623,448 B2 | 9/2003 | Slater |
| 6,638,247 B1 | 10/2003 | Selmon et al. |
| 6,638,293 B1 | 10/2003 | Makower et al. |
| 6,655,386 B1 | 12/2003 | Makower et al. |
| 6,656,195 B2 | 12/2003 | Peters et al. |
| 6,660,024 B1 | 12/2003 | Flaherty et al. |
| 6,669,709 B1 | 12/2003 | Cohn et al. |
| 6,685,648 B2 | 2/2004 | Flaherty et al. |
| 6,685,716 B1 | 2/2004 | Flaherty et al. |
| 6,694,983 B2 | 2/2004 | Wolf et al. |
| 6,695,830 B2 | 2/2004 | Vigil et al. |
| 6,709,444 B1 | 3/2004 | Makower |
| 6,719,725 B2 | 4/2004 | Milo et al. |
| 6,726,677 B1 | 4/2004 | Flaherty et al. |
| 6,746,426 B1 | 6/2004 | Flaherty et al. |
| 6,746,462 B1 | 6/2004 | Selmon et al. |
| 6,746,464 B1 | 6/2004 | Makower |
| 6,786,884 B1 | 9/2004 | DeCant, Jr. et al. |
| 6,800,085 B2 | 10/2004 | Selmon et al. |
| 6,824,550 B1 | 11/2004 | Noriega et al. |
| 6,830,577 B2 | 12/2004 | Nash et al. |
| 6,837,868 B1 | 1/2005 | Fajnsztajn |
| 6,860,892 B1 | 3/2005 | Tanaka et al. |
| 6,863,684 B2 | 3/2005 | Kim et al. |
| 6,866,676 B2 | 3/2005 | Kieturakis et al. |
| 6,884,225 B2 | 4/2005 | Kato et al. |
| 6,905,505 B2 | 6/2005 | Nash et al. |
| 6,929,009 B2 | 8/2005 | Makower et al. |
| 6,936,056 B2 | 8/2005 | Nash et al. |
| 6,942,641 B2 | 9/2005 | Seddon |
| 6,949,125 B2 | 9/2005 | Robertson |
| 6,991,617 B2 | 1/2006 | Hektner et al. |
| 7,004,173 B2 | 2/2006 | Sparks et al. |
| 7,056,325 B1 | 6/2006 | Makower et al. |
| 7,059,330 B1 | 6/2006 | Makower |
| 7,083,588 B1 | 8/2006 | Shmulewitz et al. |
| 7,094,230 B2 | 8/2006 | Flaherty et al. |
| 7,105,031 B2 | 9/2006 | Letort |
| 7,134,438 B2 | 11/2006 | Makeower et al. |
| 7,137,990 B2 | 11/2006 | Hebert et al. |
| 7,159,592 B1 | 1/2007 | Makower et al. |
| 7,179,270 B2 | 2/2007 | Makower |
| 7,191,015 B2 | 3/2007 | Lamson et al. |
| 7,229,421 B2 | 6/2007 | Jen et al. |
| 7,316,655 B2 | 1/2008 | Garibotto et al. |
| 7,377,910 B2 | 5/2008 | Katoh et al. |
| 7,413,556 B2 | 8/2008 | Zhang et al. |
| 7,465,286 B2 | 12/2008 | Patterson |
| 2001/0000041 A1 | 3/2001 | Selmon et al. |
| 2001/0056273 A1 | 12/2001 | C. |
| 2002/0029052 A1 | 3/2002 | Evans et al. |
| 2002/0052637 A1 | 5/2002 | Houser et al. |
| 2002/0103459 A1 | 8/2002 | Sparks et al. |
| 2003/0028200 A1 | 2/2003 | Berg et al. |
| 2003/0040737 A1 | 2/2003 | Merril et al. |
| 2003/0109809 A1 | 6/2003 | Jen et al. |
| 2003/0120195 A1 | 6/2003 | Milo et al. |
| 2003/0167038 A1 | 9/2003 | Yozu et al. |
| 2003/0236542 A1* | 12/2003 | Makower .................. A61F 2/95 606/167 |
| 2004/0015193 A1 | 1/2004 | Lamson et al. |
| 2004/0059280 A1 | 3/2004 | Makower et al. |
| 2004/0102719 A1 | 5/2004 | Keith et al. |
| 2004/0133225 A1 | 7/2004 | Makower |
| 2004/0158143 A1 | 8/2004 | Flaherty et al. |
| 2004/0167554 A1 | 8/2004 | Simpson et al. |
| 2004/0230156 A1 | 11/2004 | Schreck et al. |
| 2004/0249277 A1 | 12/2004 | Kato et al. |
| 2004/0249338 A1 | 12/2004 | DeCant, Jr. et al. |
| 2005/0038467 A1 | 2/2005 | Hebert et al. |
| 2005/0049574 A1 | 3/2005 | Petrick et al. |
| 2005/0171478 A1 | 8/2005 | Selmon et al. |
| 2005/0177105 A1 | 8/2005 | Shalev |
| 2005/0216044 A1 | 9/2005 | Hong |
| 2005/0261663 A1 | 11/2005 | Patterson et al. |
| 2006/0094930 A1 | 5/2006 | Sparks et al. |
| 2006/0135984 A1 | 6/2006 | Kramer et al. |
| 2006/0229646 A1 | 10/2006 | Sparks |
| 2006/0271078 A1 | 11/2006 | Modesitt |
| 2007/0083220 A1 | 4/2007 | Shamay |
| 2007/0088230 A1 | 4/2007 | Terashi et al. |
| 2007/0093779 A1 | 4/2007 | Kugler et al. |
| 2007/0093780 A1 | 4/2007 | Kugler et al. |
| 2007/0093781 A1 | 4/2007 | Kugler et al. |
| 2007/0093782 A1 | 4/2007 | Kugler et al. |
| 2007/0265596 A1 | 11/2007 | Jen et al. |
| 2008/0103443 A1 | 5/2008 | Kabrick et al. |
| 2008/0228171 A1 | 9/2008 | Kugler et al. |
| 2008/0243065 A1 | 10/2008 | Rottenberg et al. |
| 2008/0243067 A1 | 10/2008 | Rottenberg et al. |
| 2009/0088685 A1 | 4/2009 | Kugler et al. |
| 2009/0124899 A1 | 5/2009 | Jacobs et al. |
| 2009/0209910 A1 | 8/2009 | Kugler et al. |
| 2009/0270890 A1 | 10/2009 | Robinson et al. |
| 2010/0063534 A1 | 3/2010 | Kugler et al. |
| 2010/0069945 A1 | 3/2010 | Olson et al. |

FOREIGN PATENT DOCUMENTS

| | | |
|---|---|---|
| WO | 2008063621 A2 | 5/2008 |
| WO | 2009054943 A1 | 4/2009 |
| WO | 2009100129 A2 | 8/2009 |
| WO | 2009134346 A2 | 11/2009 |
| WO | 2010019241 A1 | 2/2010 |
| WO | 2010044816 A1 | 4/2010 |

OTHER PUBLICATIONS

Columbo, Antonio et al; "Treating Chronic Total Occlusions Using Subintimal Tracking and Reentry: The Star Technique." Catheterization and Cardiovascular Interventions, vol. 64: pp. 407-411 (2005).

International Search Report in PCT/US06/35244 dated Mar. 24, 2008.

Written Opinion of International Searching Authority in PCT/US06/35244 dated Mar. 24, 2008.

International Preliminary Report on Patentability in PCT/US06/35244 dated Mar. 17, 2009.

Office Action for U.S. Appl. No. 11/518,428 mailed on Jul. 1, 2010. (10 pages).

Office Action for U.S. Appl. No. 11/518,428 mailed on Jan. 28, 2010. (15 pages).

Office Action for U.S. Appl. No. 11/518,428 mailed on May 29, 2009 (12 pages).

* cited by examiner

SECTION A-A

SECTION A-A

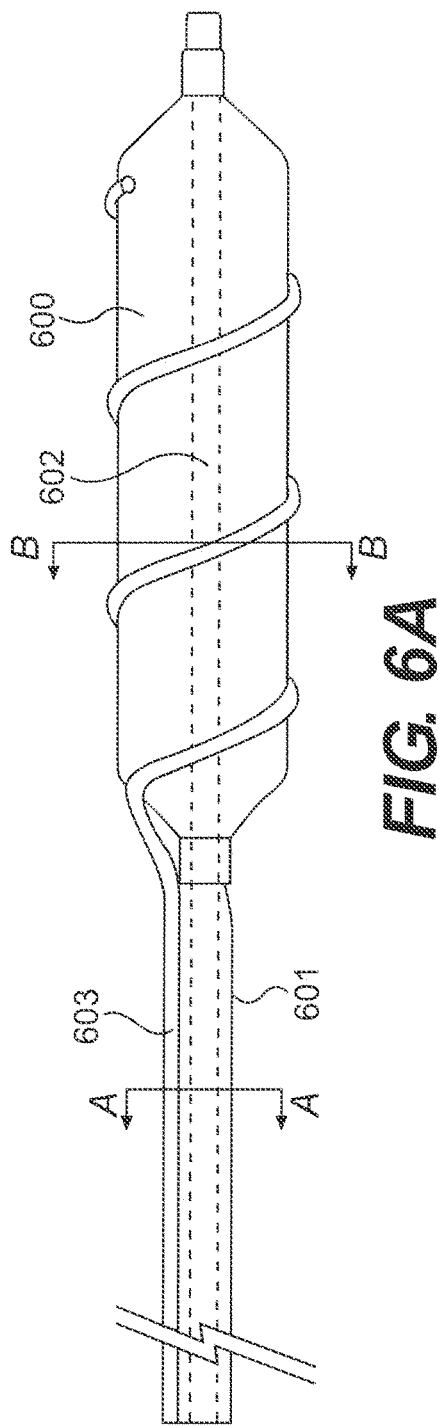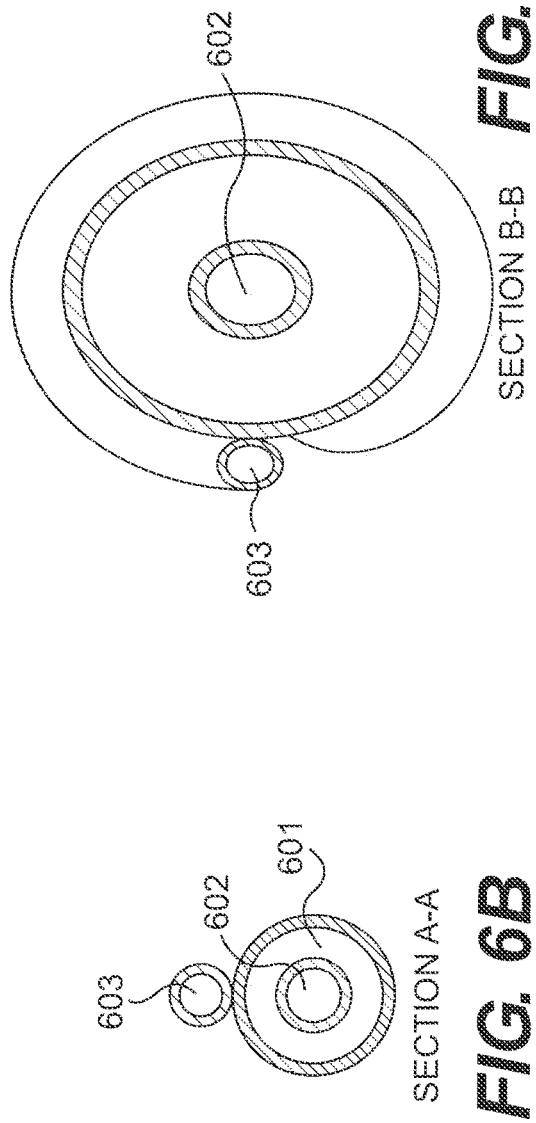

ENDOVASCULAR DEVICES AND METHODS

CROSS REFERENCE TO RELATED APPLICATIONS

This is a continuation application of U.S. application Ser. No. 17/547,442, filed Dec. 10, 2021, which is a continuation of U.S. application Ser. No. 16/396,171, filed Apr. 26, 2019, now U.S. Pat. No. 11,229,776, which is a continuation of U.S. application Ser. No. 13/037,797, filed Mar. 1, 2011, now U.S. Pat. No. 10,315,010, which is a continuation of U.S. application Ser. No. 11/518,521, filed Sep. 11, 2006, now U.S. Pat. No. 7,918,870, which claims the benefit of U.S. Provisional Application No. 60/716,287, filed Sep. 12, 2005, the contents of which are incorporated herein by reference.

FIELD OF THE INVENTION

The inventions described herein relate to devices and associated methods for the treatment of chronic total occlusions. More particularly, the inventions described herein relate to devices and methods for crossing chronic total occlusions and subsequently performing balloon angioplasty, stenting, atherectomy, or other endovascular methods for opening occluded blood vessels.

BACKGROUND OF THE INVENTION

Due to age, high cholesterol and other contributing factors, a large percentage of the population has arterial atherosclerosis that totally occludes portions of the patient's vasculature and presents significant risks to patient health. For example, in the case of a total occlusion of a coronary artery, the result may be painful angina, loss of cardiac tissue or patient death. In another example, complete occlusion of the femoral and/or popliteal arteries in the leg may result in limb threatening ischemia and limb amputation.

Commonly known endovascular devices and techniques are either inefficient (time consuming procedure), have a high risk of perforating a vessel (poor safety) or fail to cross the occlusion (poor efficacy). Physicians currently have difficulty visualizing the native vessel lumen, cannot accurately direct endovascular devices toward visualized lumen, or fail to advance devices through the lesion. Bypass surgery is often the preferred treatment for patients with chronic total occlusions, but less invasive techniques would be preferred.

SUMMARY OF THE INVENTION

To address this and other unmet needs, the present invention provides, in exemplary non-limiting embodiments, devices and methods for the treatment of chronic total occlusions. The disclosed methods and devices are particularly beneficial in crossing coronary total occlusions but may also be useful in other vessels including peripheral arteries and veins. In exemplary embodiments, total occlusions are crossed using methods and devices intended to provide a physician visualization of the occluded vascular lumen or provide physical protection for the wall of the artery to prevent perforation. In additional embodiments, devices and methods are disclosed that enhance the ability to direct and advance a guide wire within the vessel lumen.

In one embodiment, visualization of the occluded segment may be achieved by placing a subintimal device in the space around the area of the lesion. Subintimal device placement may be achieved with a subintimal device directing catheter. The catheter orients a subintimal device so that it passes along the natural delamination plane between intima and media approximating a helical path. The subintimal device directing catheter may be an inflatable balloon catheter having proximal and distal ends with two wire lumens. One lumen accepts a conventional guide wire while the second lumen accepts the subintimal device. In an alternative embodiment, the wire directing catheter may be a guide catheter with distal geometry that steers the subintimal device with the appropriate orientation to enter the subintimal space and advance in a helical pattern around the lesion. Visualization of the artery may be achieved as the subintimal device encircles the artery with each helical turn. The wire's shape may approximate the inside diameter of the lumen and also may define axial bends or tortuosity in the vessel. The subintimal device may further serve the purpose of providing mechanical protection for the artery from perforation or damage from subsequently used devices. Once the subintimal device is in place around the lesion, a number of conventional techniques may be used to cross the lesion including for example stiff guide wires, lasers, ultrasonic energy, mechanical dissection, and atherectomy. Alternatively, a guide wire support device may be used that has the ability to rotationally engage the lesion through helical corkscrew profile on the outside surface. An additional aspect may be the ability to independently steer or direct a guide wire support catheter within the vessel lumen while maintaining the ability to rotate, engage, and advance the corkscrew catheter shaft.

The subintimal device may have a mechanism that rotationally engages the arterial tissues and helps drive the wire through the subintimal space. This mechanism may allow the physician to torque the wire at its proximal end, engage the subintimal tissues and achieve wire advancement. This aspect of the wire may for example include a raised helical corkscrew protrusion on the outside surface of the wire. An additional aspect of the subintimal device may include an atraumatic tip that aids in the prevention of arterial perforation.

BRIEF DESCRIPTION OF THE DRAWINGS

It is to be understood that both the foregoing summary and the following detailed description are exemplary. Together with the following detailed description, the drawings illustrate exemplary embodiments and serve to explain certain principles. In the drawings.

FIGS. 6A-C show schematic and sectional views of a subintimal device directing balloon catheter;

DETAILED DESCRIPTION OF EXEMPLARY EMBODIMENTS

Figure 1A:
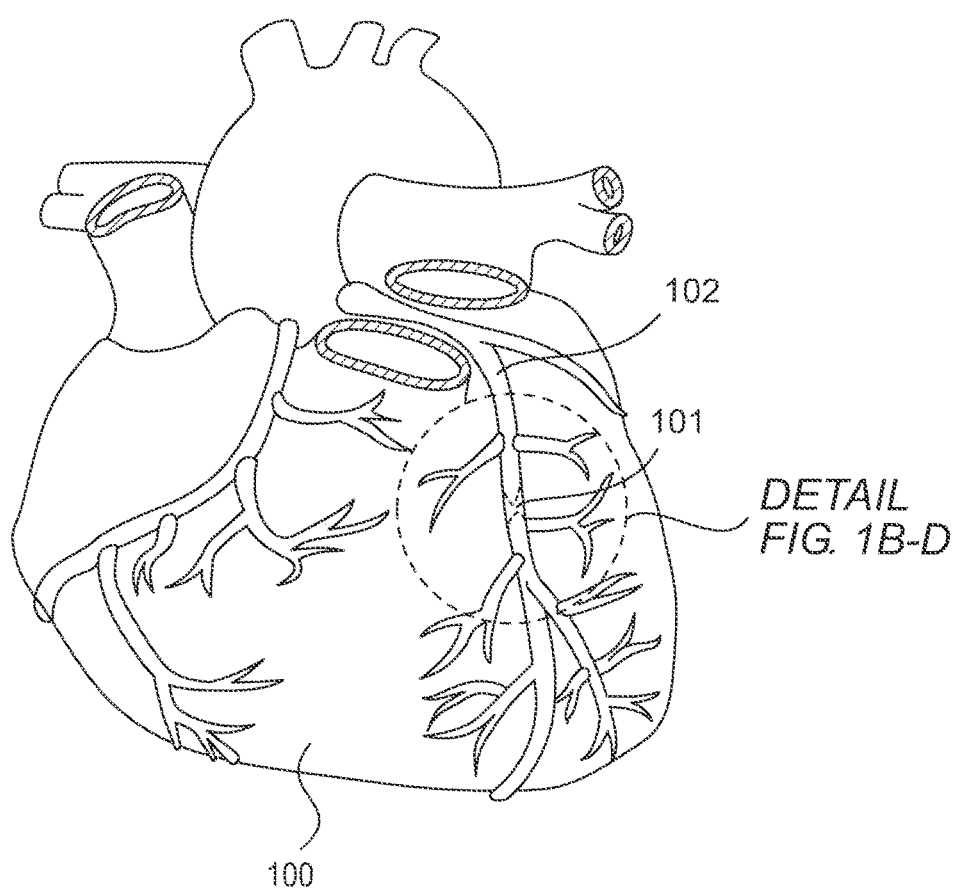
FIG. 1A shows an illustration of a heart showing a coronary artery that contains a chronic total occlusion and illustrates the position of the detail section shown in FIGS. 1B-D.
Figure 1B:
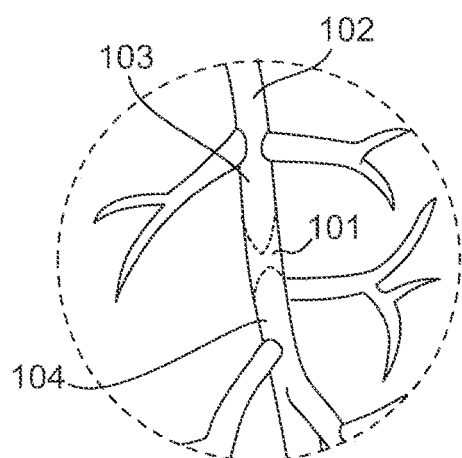
FIG. 1B is an illustration showing a magnified view of a chronic total occlusion.
Figure 1C:
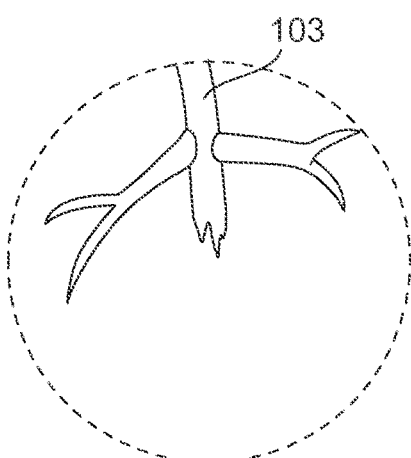
FIG. 1C is a representation of fluoroscopy image of the chronic total occlusion.

The following detailed description should be read with reference to the drawings in which similar elements in different drawings are numbered the same. The drawings, which are not necessarily to scale, depict illustrative embodiments and are not intended to limit the scope of the invention.

Referring to FIG. 1, a diseased heart 100 including a chronic total occlusion 101 of a coronary artery 102. FIG. 1B shows a magnified view of a chronic total occlusion 101 within coronary artery 102. The figure shows arterial sections both proximal 103 and distal 104 of lesion 101. The proximal segment 103 may be easily accessed using endovascular devices and has adequate blood flow to supply the cardiac muscle. The distal segment 104 is not easily accessed with interventional devices and has significantly reduced blood flow as compared to proximal segment 103. A commonly performed diagnostic procedure called an angiogram infuses a radiopaque fluid into the arterial bloodstream through a percutaneously placed angiography catheter and records two dimensional images of the arterial pathways using a fluoroscope. FIG. 1C shows an example of an angiographic image of a chronic total occlusion. It is common that the angiogram allows a physician to visualize the proximal segment 103 but does not allow visualization of the distal segment.

Figure 1D:
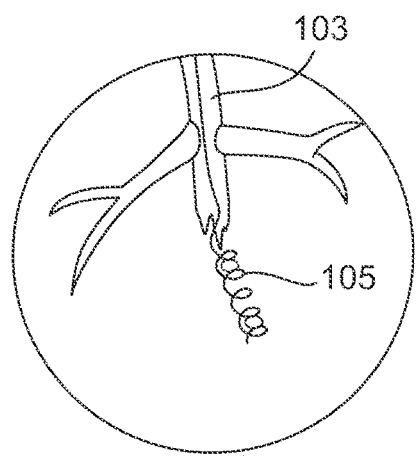
FIG. 1D is a representation of a fluoroscopy image with a subintimal device in position around the lesion.

An aspect of the disclosure enhances arterial visualization by placing a radiopaque device within the subintimal space around the chronic total occlusion. For the purpose of description, not limitation, the term "subintimal device" will henceforth refer to the wire placed within the subintimal space for purposes of visualization, protecting the vessel, or other purpose, while the term "guide wire" will refer to the wire placed within the vascular lumen for purposes of advancing diagnostic and therapeutic devices within the lumen. FIG. 1D is an additional angiographic image example showing proximal arterial segment 103 and subintimal device 105 positioned concentrically around the chronic total occlusion and within the subintimal space. The subintimal device 105 defines the approximate inside diameter of the artery and also defines axial bends or tortuosity in the vessel.

Figure 2:
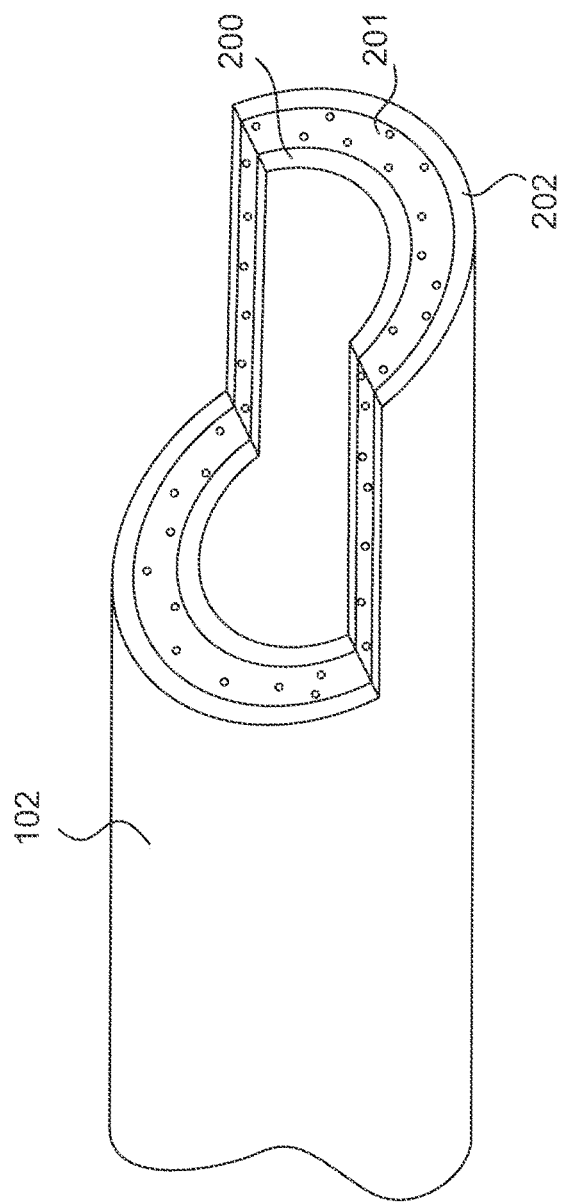
FIG. 2 is a schematic representation of a coronary artery showing the intimal, medial and adventitial layers.

FIG. 2 shows coronary artery 102 with intimal layer 200 (for sake of clarity, the multi layer intima is shown as a single homogenous layer). Concentrically outward of the intima is the medial layer 201 (which also is comprised of more than one layer but is shown as a single layer). The transition between the external most portion of the intima and the internal most portion of the media is referred to as the subintimal space. The outermost layer of the artery is the adventitia 202.

One aspect of the disclosure is the design of the subintimal device. Embodiments of the subintimal device distal tip are described in FIGS. 3A-D where the tip includes an atraumatic element. Examples of atraumatic elements are a ball tip 301, looped tip 302 and directional tip 303. These elements are intended to distribute axial forces over larger areas of tissue and may reduce the chance of vessel perforation. An additional aspect of the directional tip 303 is ability to torsionally direct the tip and control the path of the device through the subintimal space. The ball tip 301 may be formed from a suitable metallic material including but not limited to stainless steel, silver solder, or braze. The ball tip 301 may also be formed from suitable polymeric materials or adhesives including but not limited to polycarbonate, polyethylene or epoxy. The loop tip 302 and directional tip 303 may be created during the manufacturing process (for example by heat setting or mechanical deformation) or the tip may be shaped (for example by mechanical deformation) by the physician.

Figure 3A:
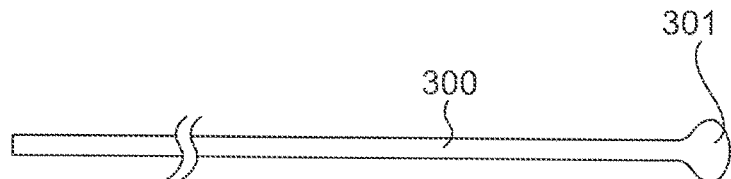
FIGS. 3A-D illustrate atraumatic tip configurations of a subintimal device.
Figure 3B:
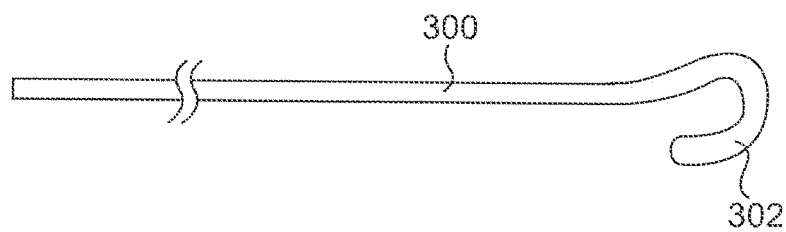
Figure 3C:
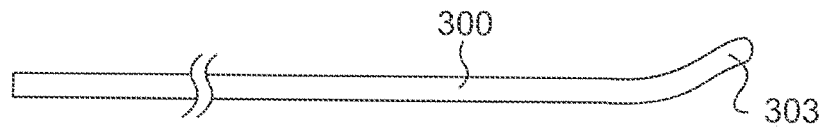
Figure 3D:
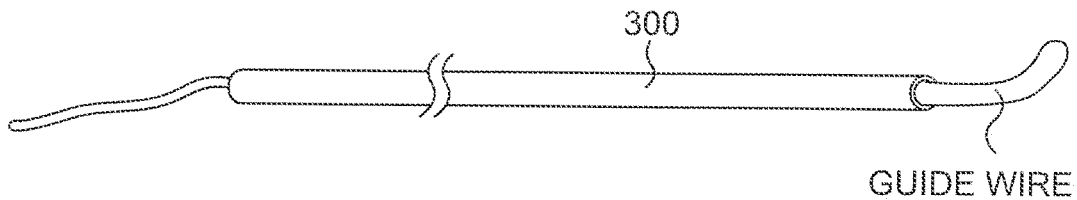

In an alternative embodiment, FIG. 3D describes a subintimal device where the hollow internal diameter of the body 300 defines a guide wire lumen. The lumen has proximal and distal ends and can accept a guide wire. The guide wire provides an atraumatic element at its distal end and also provides a mechanism for rotationally steering the subintimal device through the subintimal space. The guide wire may be pushed forward by the subintimal device through an element (i.e. bearing surface) at the proximal or distal end of the subintimal device. This element may provide interference in the axial direction while allowing for relative rotation between the subintimal device and guide wire. An example of a bearing surface may be a collar crimped to the distal end of the guide wire with an outside diameter larger in dimension than the guide wire lumen within the subintimal device.

Figure 4A:
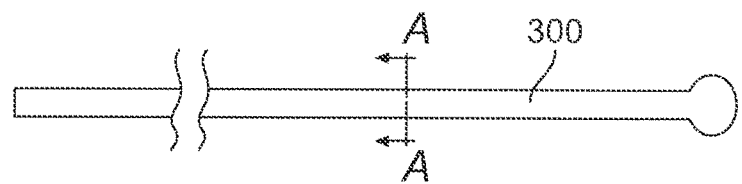
FIG. 4A is a schematic illustration of a subintimal device.
Figure 4B:
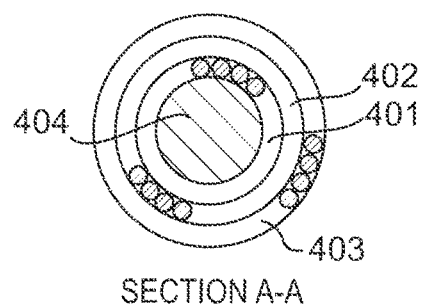
FIGS. 4B and 4D are cross-sectional views of the subintimal device shown in FIG. 4A taken along line A-A.
Figure 4C:
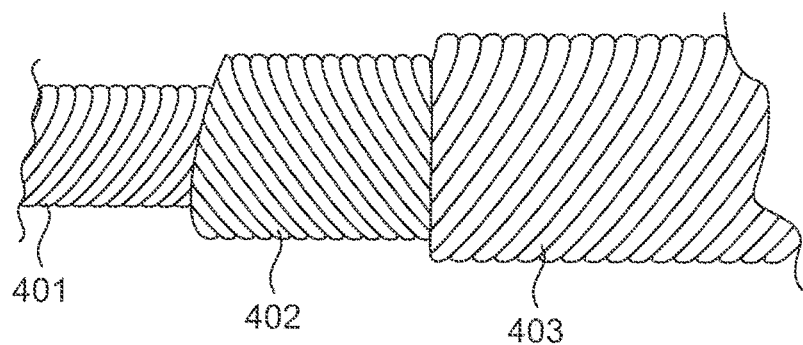
FIG. 4C shows a subintimal device body embodiment describing a multi layered coil construction.

An additional aspect of the subintimal device is the construction of the device body. The flexibility and torquability of the device body can affect the physician's ability to achieve a helical and subintimal path around the lesion. The sectional view shown in FIG. 4B describes a device body made of a multitude of independent coils 401-403 concentrically wound in opposing directions. These coils can diametrically interact (for example internal coil diametrically expands while the external coil diametrically contracts) with an applied torque. This interaction can provide torsional strength while maintaining axial flexibility. The device body may have sections of increased or decreased torsional or axial rigidity. For example, the proximal most portion of the subintimal device may be formed from a solid stainless steel tube and the distal most section may have the aforementioned multiple coil construction. Alternatively, the device core 404 may be hollow or may contain a permanently fixed wire within its internal lumen. A permanently fixed wire may provide an increase in axial or torsional stiffness. A permanently fixed wire may also have a tapering cross section to increase the distal flexibility. The lumen within a hollow subintimal device may also be used for the insertion of a guide wire. Coils 401-403 and core wire 404 may be made of a suitable metallic or polymeric material including but not limited to stainless steel, nickel titanium, platinum or ultra high molecular weight polyethylene.

Figure 4D:
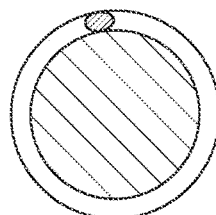
Figure 4E:
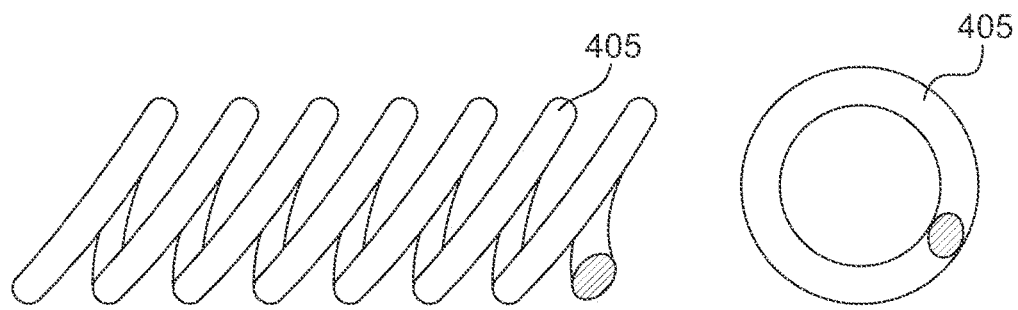
FIGS. 4E-G show alternative subintimal device body embodiments.

In an alternative embodiment, a subintimal device body construction is shown in FIG. 4D where a single coil may be positioned over an internal core. The additional embodiment shown in FIG. 4E shows a single open wound coil 405 as the subintimal device body.

Figure 4F:
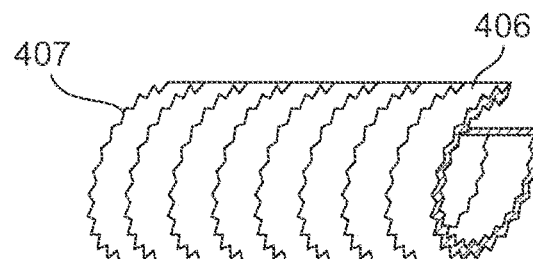
Figure 4G:
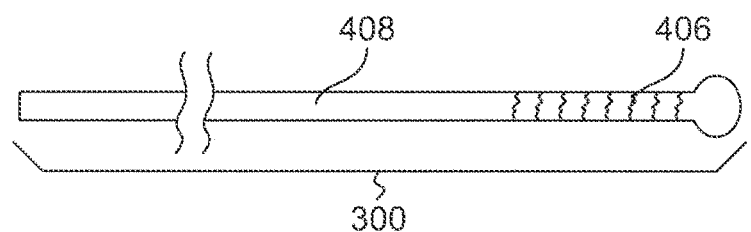

In another embodiment, the subintimal device body may be constructed in part or in total of a single layer coil with geometric features along the coil length that allow adjacent coils to engage (for example mechanical engagement similar to the teeth of a gear). FIG. 4F shows coil 406 closely wound such that the multitude of teeth 407 along the coil edges are in contact such that the peaks of one coil falls within the valleys of the adjacent coil. A conventional coil reacts to an applied torsional load by diametrically expanding or contracting, thus forcing the wire surfaces within a turn of the coil to translate with respect to its neighboring turn. The construction of coil 406 resists the translation of wire surfaces within the coil thus resisting the diametric expansion or contraction (coil deformation). An increased resistance to coil deformation increases the torsional resistance of the device body while the coiled construction provides axial flexibility. An exemplary construction may include a metallic tube where the coil pattern 406 and teeth 407 are cut from the tube diameter using a laser beam. FIG. 4G shows subintimal device body 300 that is for example continuous metallic tube with distal laser cut coil segment 406 and proximal solid tube 408. Tube materials include but are not limited to stainless steel and nickel titanium. Alternatively, the coil 406 may be wound from a continuous wire. The wire has a cross section that for example has been mechanically deformed (stamped) to form the teeth and allow coil engagement.

Figure 5A:
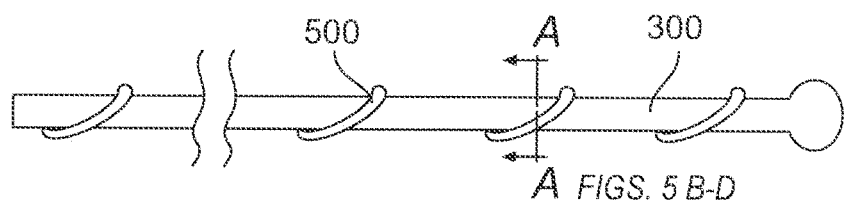
FIGS. 5A-D show embodiments of subintimal devices having various surface features.
Figure 5B:
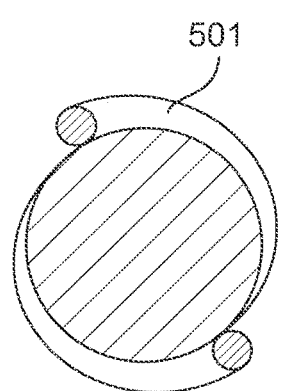
Figure 5C:
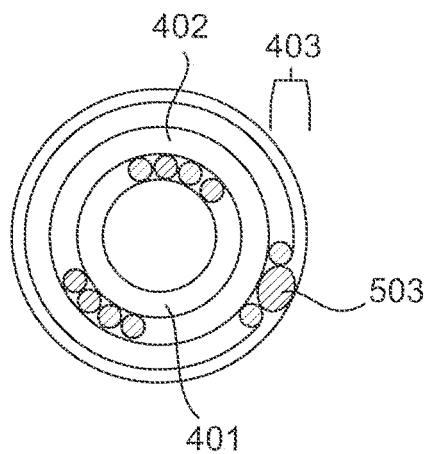
Figure 5D:
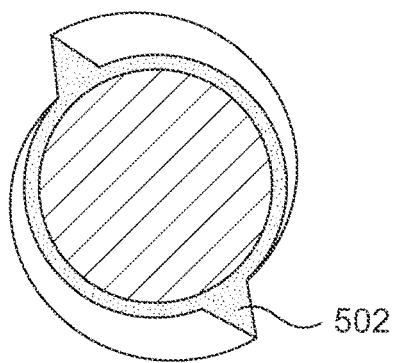

Another aspect of the disclosure is the exterior surface of the subintimal device. FIG. 5A shows an embodiment where the device body 300 has an external corkscrew 500 that has the ability to rotationally engage the arterial tissues and help drive the device through the subintimal space. FIG. 5B describes an embodiment where one or more round corkscrew members 501 are concentrically wound on the outside of the body 300. Alternatively, FIG. 5C describes a multilayer device body with layers 401-403 where corkscrew member 503 h element of larger cross sectional area wound within the external concentric coil 403. Alternative corkscrew embodiments may include triangular, square, or her cross sections that may aid in tissue engagement and subintimal device advancement. In another exemplary embodiment shown in FIG. 5D, a polymer tube with corkscrew profile 502 may be concentrically positioned around device body 300. Withdrawal of a subintimal device that rotationally engages the arterial tissues may be completed by rotating the device in the opposite direction thus driving the device back out of the subintimal space.

Figure 7:
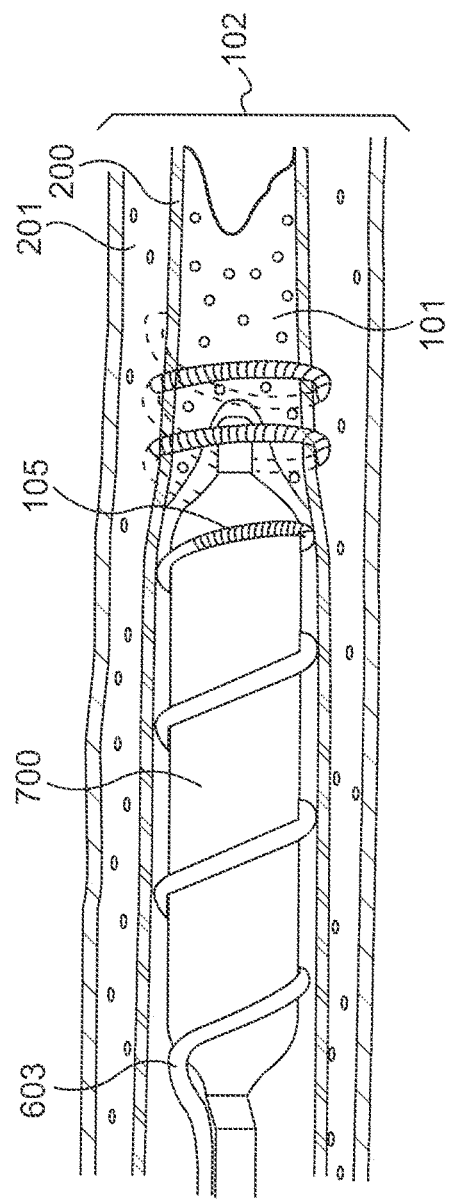
FIG. 7 is a sectional view of a totally occluded vessel with a subintimal device directing balloon catheter inflated proximal to the lesion and a subintimal device advanced partially around the lesion.

An additional aspect of the disclosure may be a device that directs the subintimal device through the intima and into the subintimal space. In one embodiment shown in FIGS. 6A-C, a balloon catheter with distal balloon 600 and proximal balloon inflation lumen 601 may be advanced over a guide wire that traverses guide wire lumen 602. Once in position us proximal of the chronic total occlusion, the balloon may be inflated within the vessel lumen to direct the subintimal device lumen 603 toward the vessel wall at orientation for subintimal device penetration into the intima and through the subintimal space. FIG. 7 shows subintimal balloon catheter 700 positioned and inflated within coronary artery 102. Subintimal device 105 has been advanced through subintimal device lumen 603 and positioned concentrically outside the chronic total occlusion 101, outside the intimal layer 200, and inside the medial layer 201 and may be contained in the subintimal space.

An alternative method for achieving subintimal position may use a guide catheter that has distal geometry that directs the device toward the interior vessel wall with the appropriate orientation. An example may be a guide catheter that has a permanently formed curve at the distal end suitable for device advancement. Alternatively, the catheter may be actively steerable so that the physician can choose an orientation insitu.

Figure 8A:
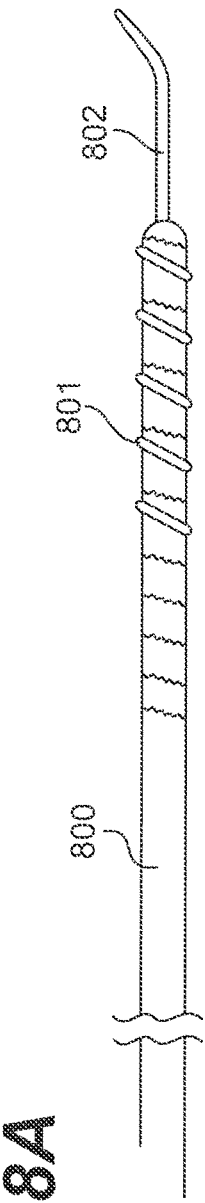
FIGS. 8A-C show an embodiment of an advancement device used to advance devices across the lesion within the vessel lumen.
Figure 8B:
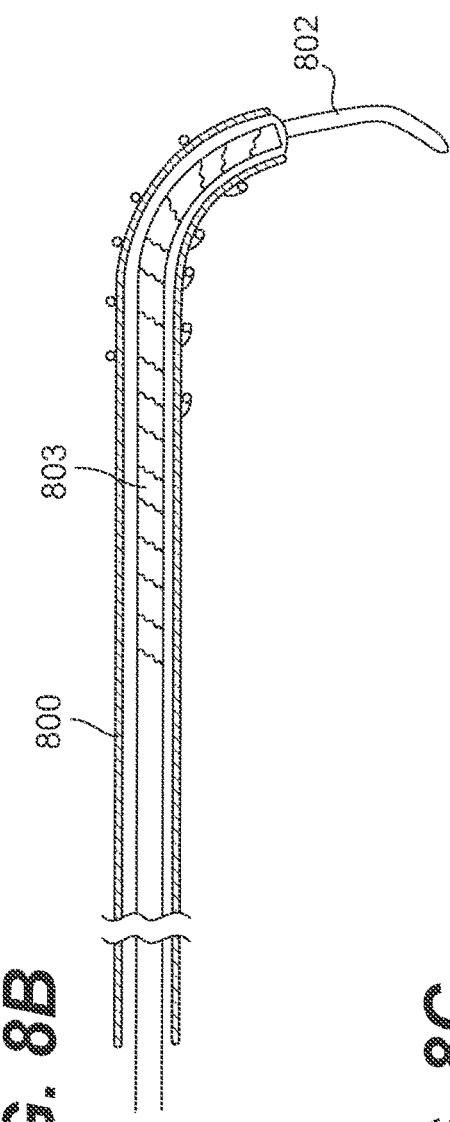
Figure 8C:
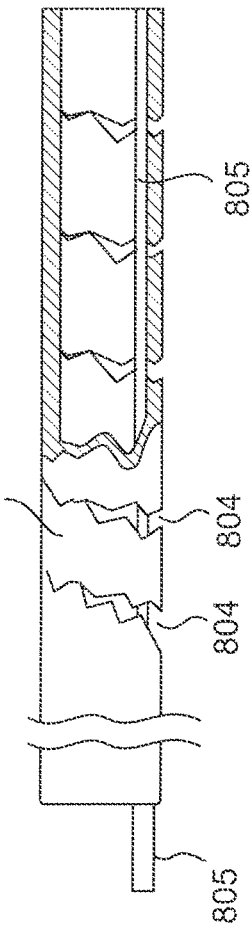

An additional aspect of the disclosure is the method and devices used to advance devices across the lesion within the vessel lumen. A number of conventional techniques may be used including stiff guide wires, lasers, ultrasonic energy, mechanical dissection, atherectomy and other techniques known to those skilled in the art. One aspect of the disclosure may be a guide wire support device intended to enhance guide wire stiffness, engage the lesion thus providing axial support, and allow the physician to direct the tip of the guide wire. FIGS. 8A-8C describe a wire support device where external shaft 800 may be comprised of one or more coils intended to provide axial flexibility and torsional rigidity. External helical profile 801 exists on the outside of the external shaft 800 and may provide mechanical engagement with the lesion. FIG. 8B shows a partial sectional view of the wire support device where internal shaft 803 resides concentrically within the external shaft. The internal shaft 803 contains a guide wire lumen capable of accepting conventional guide wires. The internal shaft may also be comprised of one or more coils. FIG. 8C shows a partial enlarged view of the internal shaft 803 where a gap 804 between adjacent coils allow articulation of the shaft upon proximal withdrawal of actuation wire 805. External shaft 800 can freely rotate with respect to internal shaft 803 when the shaft is in the straight and actuated positions.

From the foregoing, it will be apparent to those skilled in the art that the present invention provides, in exemplary non-limiting embodiments, devices and methods for the treatment of chronic total occlusions. Further, those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method of treating an occlusion of a blood vessel, comprising:
    advancing an intravascular device within a lumen of the blood vessel to a position adjacent the occlusion, wherein the intravascular device comprises:
        an elongate shaft defining a central longitudinal axis;
        a first lumen extending to a distal opening at a distal end of the elongate shaft;
        a second lumen extending to a distal opening located proximal of the distal end of the elongate shaft; and
        an inflatable balloon secured to the elongate shaft, the inflatable balloon including an expandable portion;
    inflating the inflatable balloon to orient the distal opening of the second lumen toward an intimal layer of a wall of the blood vessel; and
    thereafter, advancing a subintimal device through the second lumen and into a subintimal space of the blood vessel proximal of the distal end of the elongate shaft.

2. The method of claim 1, further comprising:
    advancing the subintimal device distally within the subintimal space of the blood vessel to a position distal of the intravascular device.

3. The method of claim 2, wherein the subintimal space is disposed outside of the intimal layer of the wall of the blood vessel and inside of a medial layer of the wall of the blood vessel.

4. The method of claim 1, further comprising:
advancing the subintimal device helically around the occlusion of the blood vessel.

5. The method of claim 1, wherein the distal opening of the first lumen is centered on the central longitudinal axis.

6. The method of claim 1, wherein advancing the intravascular device within the lumen of the blood vessel further comprises advancing the intravascular device over a guidewire disposed within the first lumen.

7. The method of claim 1, wherein the subintimal device comprises a device body having a corkscrew member extending radially outward from an outer surface of the device body.

8. The method of claim 7, wherein the corkscrew member is configured to rotationally engage tissue to drive the subintimal device through the subintimal space.

9. A method of treating an occlusion of a blood vessel, comprising:
advancing an intravascular device within a lumen of the blood vessel to a position adjacent the occlusion, wherein the intravascular device comprises:
an elongate shaft defining a central longitudinal axis;
a first lumen extending to a distal opening at a distal end of the elongate shaft; and
a second lumen extending to a distal opening located along a distal end region of the intravascular device proximal of the distal end of the elongate shaft;
urging the distal end region of the intravascular device toward an intimal layer of a wall of the blood vessel to position the distal opening of the second lumen against the intimal layer of the wall of the blood vessel; and
thereafter, advancing a subintimal device through the second lumen and into a subintimal space of the blood vessel proximal of the distal end of the elongate shaft.

10. The method of claim 9, further comprising:
advancing the subintimal device distally within the subintimal space of the blood vessel to a position distal of the intravascular device.

11. The method of claim 9, further comprising:
advancing the subintimal device helically around the occlusion of the blood vessel.

12. The method of claim 9, wherein the distal opening of the first lumen is centered on the central longitudinal axis.

13. The method of claim 12, wherein advancing the intravascular device within the lumen of the blood vessel further comprises advancing the intravascular device over a guidewire disposed within the first lumen.

14. A method of treating an occlusion of a blood vessel, comprising:
advancing an intravascular device within a lumen of the blood vessel to a position adjacent the occlusion, wherein the intravascular device comprises:
an elongate shaft defining a central longitudinal axis;
an inflatable balloon secured to the elongate shaft, the inflatable balloon including an expandable portion;
a first lumen extending coaxially with the central longitudinal axis to a distal opening positioned distal of the expandable portion of the inflatable balloon;
a second lumen extending along an exterior of the expandable portion of the inflatable balloon to a distal opening positioned intermediate a proximal end of the expandable portion and a distal end of the expandable portion; and
inflating the inflatable balloon to expand the expandable portion and orient the distal opening of the second lumen toward an intimal layer of a wall of the blood vessel;
after expanding the expandable portion, advancing a subintimal device through the second lumen and into a subintimal space within the wall of the blood vessel.

15. The method of claim 14, wherein advancing the intravascular device within the lumen of the blood vessel further comprises advancing the intravascular device over a guidewire disposed within the second lumen.

16. The method of claim 14, wherein the second lumen extends axially along an outer surface of the elongate shaft.

17. The method of claim 14, wherein the second lumen extends helically around the expandable portion of the inflatable balloon.

18. The method of claim 14, further comprising:
advancing the subintimal device helically around the occlusion of the blood vessel within the subintimal space.

19. The method of claim 18, wherein advancing the subintimal device helically around the occlusion of the blood vessel within the subintimal space includes positioning the subintimal device concentrically around the occlusion of the blood vessel within the subintimal space.

20. The method of claim 14, wherein the subintimal device comprises a device body having a corkscrew member extending radially outward from an outer surface of the device body.

* * * * *